US006772854B2

(12) United States Patent
Wubker

(10) Patent No.: US 6,772,854 B2
(45) Date of Patent: Aug. 10, 2004

(54) DEVICE AND METHOD FOR INSERTING ACOUSTIC DAMPERS INTO EARPHONES

(75) Inventor: John James Wubker, Lindenhurst, IL (US)

(73) Assignee: Shure Incorporated, Niles, IL (US)

( * ) Notice: Subject to any disclaimer, the term of this patent is extended or adjusted under 35 U.S.C. 154(b) by 13 days.

(21) Appl. No.: 10/105,641

(22) Filed: Mar. 25, 2002

(65) Prior Publication Data

US 2002/0139607 A1 Oct. 3, 2002

Related U.S. Application Data

(60) Provisional application No. 60/279,185, filed on Mar. 27, 2001.

(51) Int. Cl.[7] ............................ A61B 7/02; H04R 25/02

(52) U.S. Cl. ........................ 181/135; 181/130; 381/329

(58) Field of Search .......................... 29/729, 734, 758, 29/764, 270, 280, 281.1, 283.5; 181/135, 134, 133, 130, 129, 136; 381/324, 380, 382, 68.6, 153, 154, 158, 328, 329; 128/864, 865, 867

(56) References Cited

U.S. PATENT DOCUMENTS 3,565,069 A * 2/1971 Miller ........................ 128/867
3,800,791 A * 4/1974 Visor ......................... 181/135
4,349,082 A * 9/1982 Gastmeier .................... 181/130
4,540,063 A 9/1985 Ochi et al.
4,756,312 A * 7/1988 Epley ......................... 381/328
4,774,933 A * 10/1988 Hough et al. ............... 381/329
4,850,023 A 7/1989 Yarush
5,113,967 A * 5/1992 Killion et al. .............. 181/132
5,220,918 A * 6/1993 Heide et al. .................. 600/25
6,055,319 A * 4/2000 Shennib et al. ............. 381/328
6,148,821 A * 11/2000 Falco .......................... 128/864
6,286,622 B1 * 9/2001 Tiemann ..................... 181/135
2003/0159878 A1 * 8/2003 Hakansson et al. ......... 181/135

FOREIGN PATENT DOCUMENTS

JP 405083797 A 4/1993

* cited by examiner

*Primary Examiner*—Shih-Yung Hsieh
*Assistant Examiner*—Edgardo San Martin
(74) *Attorney, Agent, or Firm*—Banner & Witcoff , Ltd.

(57) ABSTRACT

The present invention relates generally to a device and method for inserting and retaining an acoustical damper in a sound port for in-ear monitoring systems. In particular, a device having an insertion rod for guiding an acoustical damper into the opening of a sound port, and displacement members for forming retaining notches at the opening of the sound port, whereby the retaining notches retain the acoustical damper in the sound port.

10 Claims, 5 Drawing Sheets

FIG.7
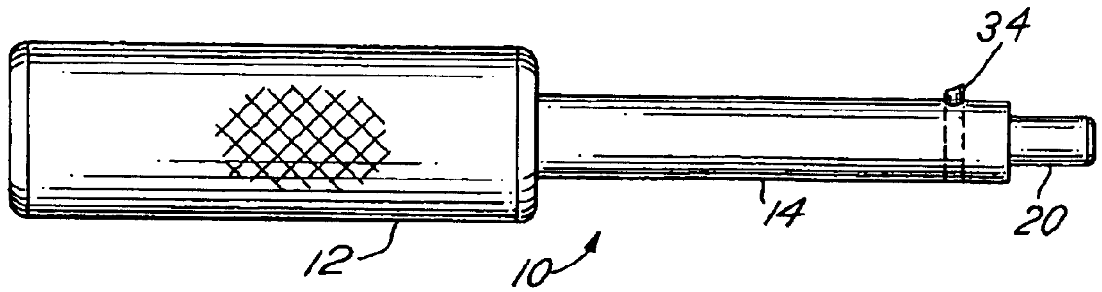
FIG.8
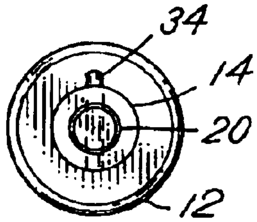
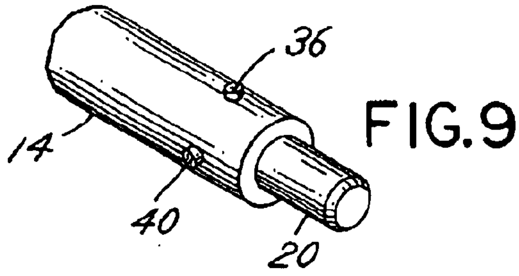
FIG.9
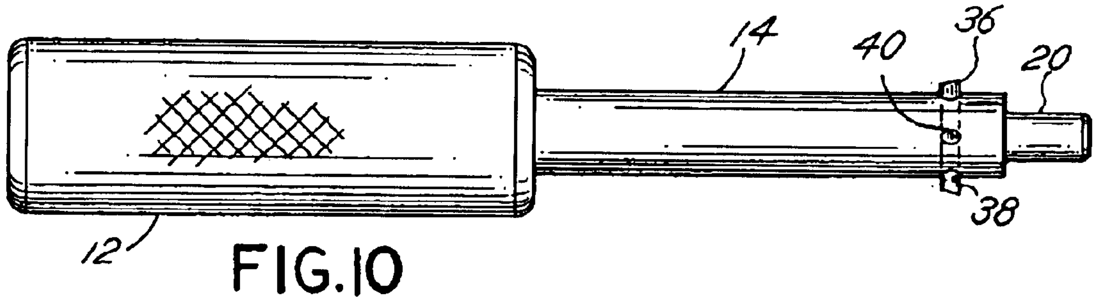
FIG.10
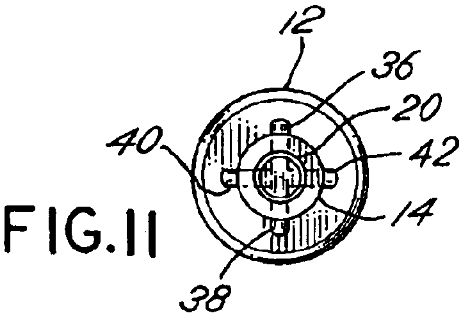
FIG.11

FIG.12
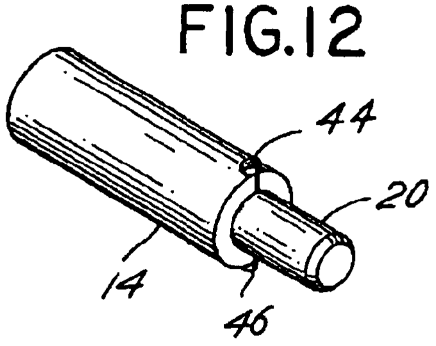
FIG.13
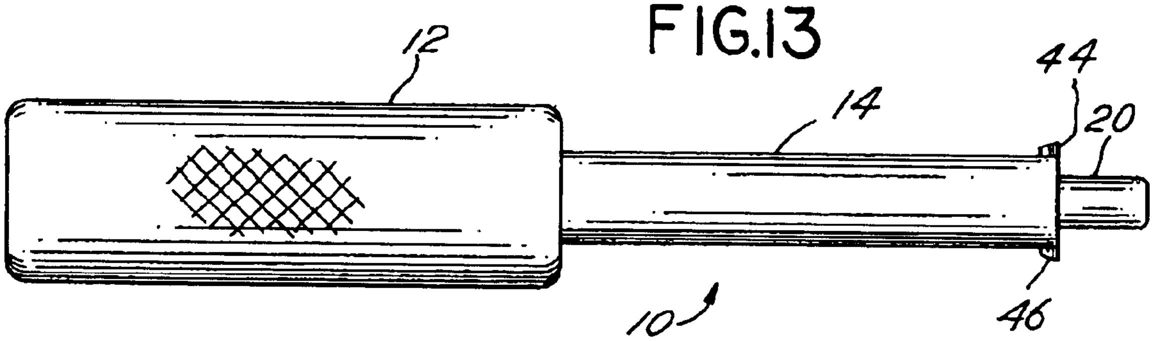
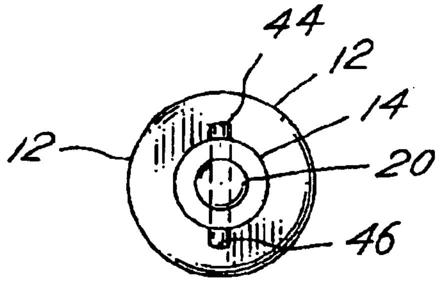
FIG.14

FIG.15
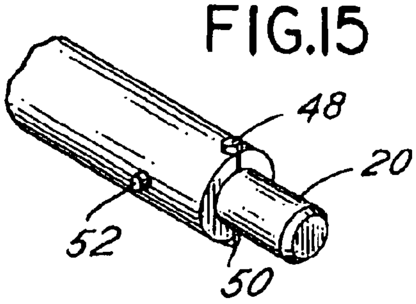
FIG.16
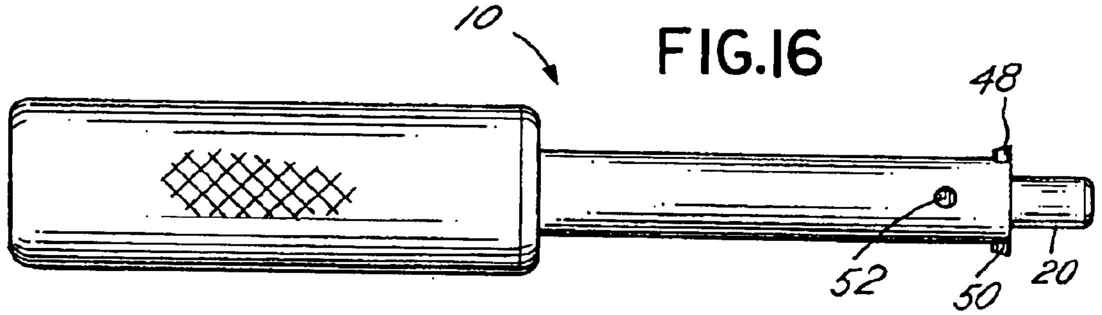
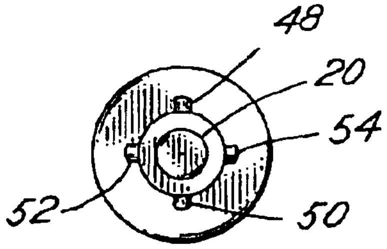
FIG.17
FIG.18
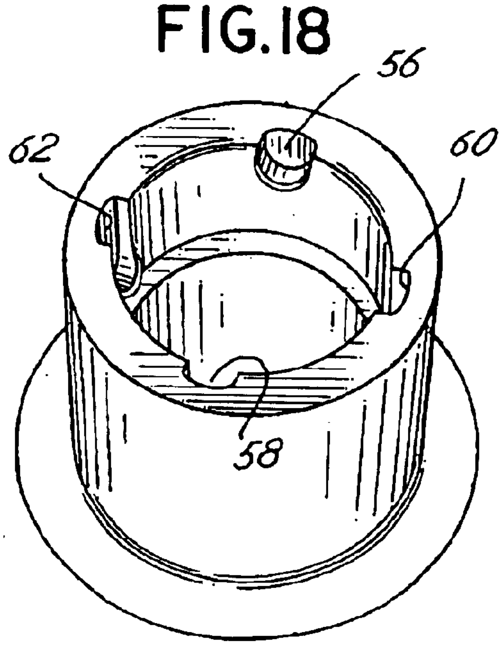

DEVICE AND METHOD FOR INSERTING ACOUSTIC DAMPERS INTO EARPHONES

RELATED APPLICATIONS

This application is based on, and claims the benefit of, co-pending U.S. Provisional Application Serial No. 60/279,185, filed on Mar. 27, 2001, and entitled "A Device and Method for Inserting Acoustic Dampers Into Earphones."

FIELD OF THE INVENTION

The present invention relates generally to in-ear monitoring systems and more particularly, to a device and method for inserting and retaining an acoustical damper in a sound port for in-ear monitoring systems.

BACKGROUND OF THE INVENTION

Personal or "in-ear" monitoring systems are increasingly utilized by musicians, recording studio engineers, and live sound engineers to monitor performances on stage and in the recording studio. In-ear systems deliver a music mix directly to the musicians or engineer's ears without competing with other stage or studio sounds. These systems provide the musician or engineer with increased control over the balance and volume of instruments and tracks, and serve to protect the musician or engineer's hearing through better sound quality at a lower volume setting. In-ear monitoring systems have replaced conventional floor monitor wedges or speakers, and in turn, have significantly changed the way musicians and sound engineers work on stage and in the studio.

In-ear systems typically utilize earphones that rest in the ear canal of the listener. Typical earphones have a driver mounted within a housing. Sound is conveyed from the output of the driver through a cylindrical sound port that is typically constructed of Acrylonitrile Butadiene Styrene (ABS) plastic. A suitable ear mold, such as slow recovery foam plugs, couple the sound port to the ear cavity of the listener. These earphones, however, generally have a flat frequency response with an un-damped peak across a known frequency range. The un-damped frequency response results in poor sound quality and often results in user discomfort where complex sounds have an energy concentration in the vicinity of the un-damped peak.

In order to regulate or smooth the frequency response and increase the performance of the earphone, earphones utilize acoustical dampers that that are located within the cylindrical sound port of the earphone. Typical acoustical dampers are stainless steel cylindrical tubes containing a mesh or matrix material that allows sound to pass therethrough. The matrix material provides acoustical resistance to the sound passing through the damper, resulting in a shaped frequency range response. Because of the acoustical damper's improvement in sound quality and earphone performance, acoustical dampers are essential elements of in-ear monitoring systems.

Conventional methods of inserting and retaining the acoustical damper within the cylindrical sound port include press fitting the damper into the sound port, inserting a wedge to retain the damper within the sound port, or clipping the damper to the sound port. Problems arise, however, with these conventional methods. For example, press fitting requires the application of pressure to force the stainless steel cylindrical damper into the plastic cylindrical sound port. The force applied during press fitting may create cracks in the plastic sound port—possibly resulting in improper seating of the damper within the sound port. Similarly, the use of wedges to retain the damper within the sound port often leads to cracks in the plastic sound port since insertion of the wedge creates a force that exceeds the tensile strength of the plastic sound port. Moreover, transport or handling of the earphones over time may exacerbate the cracks in the plastic sound port, possibly causing the damper to shake loose from the earphone and fall into the ear canal of the user. Additionally, when clips are utilized to retain the damper within the sound port, handling or transport of the earphone over time can cause the clip to loosen. The damper may shift within the sound port and cause a reduction in sound quality.

The aforementioned problems associated with the conventional methods of inserting and retaining the damper within the earphone can result in a defective earphone, and increased manufacturing costs. Accordingly, there exists a genuine need for a method of inserting and retaining a acoustical damper in a sound port that overcomes the disadvantages of the conventional methods. The present invention solves the aforementioned problems.

BRIEF SUMMARY OF THE INVENTION

One aspect of the present invention relates to a device for inserting an acoustical damper in a sound port of an earphone. In an exemplary embodiment of the present invention, the insertion device has a handle connected to an insertion rod. The insertion rod contains a damper retaining rod and displacement members. In operation, the retaining rod holds an acoustical damper on the insertion rod as the damper is guided into the opening of the sound port. When the damper is positioned completely within the sound port, the displacement members contact the opening of the sound port. As force is applied with the insertion device on the sound port, the displacement members form retaining notches at the opening of the sound port. The retaining notches retain the acoustical damper within the sound port. Another aspect of the present invention relates to a method of inserting and retaining an acoustical damper in a sound port of an earphone by providing a damper insertion device having a retaining rod and displacement members; placing an acoustical damper on the retaining rod of the insertion rod; guiding the acoustical damper into an opening of a cylindrical sound port with the insertion device; positioning the damper completely within the sound port with the insertion device; contacting the displacement members with the cylindrical opening of the sound port; applying pressure with the displacement members to form retaining notches in the sound port; retaining the acoustical damper in the sound port with the retaining notches.

These and other features of the present invention may best be understood with reference to the accompanying drawings and in the following detailed description of the invention.

BRIEF DESCRIPTION OF THE DRAWINGS

Other objects, features, and advantages of the present invention will become apparent from the detailed description of the invention that follows, when considered in light of the accompanying drawings. In the drawings, the figures have the following general nature:

FIG. 7 is a side view of another embodiment of the insertion device of the present invention;

FIG. 8 is an end view of the of the insertion device shown in FIG. 7;

FIG. 9 is a partial isometric view of another embodiment of the insertion device of the present invention;

FIG. 10 is a side view of the insertion device shown in FIG. 9;

FIG. 11 is a end view of the insertion device shown in FIG. 9;

FIG. 12 is a partial isometric view of another embodiment of the insertion device of the present invention;

FIG. 13 is a side view of the insertion device shown in FIG. 12;

FIG. 14 is an end view of the insertion device shown in FIG. 12;

FIG. 15 is partial isometric of another embodiment of the insertion device of the present invention;

FIG. 16 is a side view of the insertion device shown in FIG. 15;

FIG. 17 is an end view of the insertion device shown in FIG. 15; and

FIG. 18 depicts an acoustical damper retained in a sound port.

DETAILED DESCRIPTION OF THE INVENTION

Figure 1:
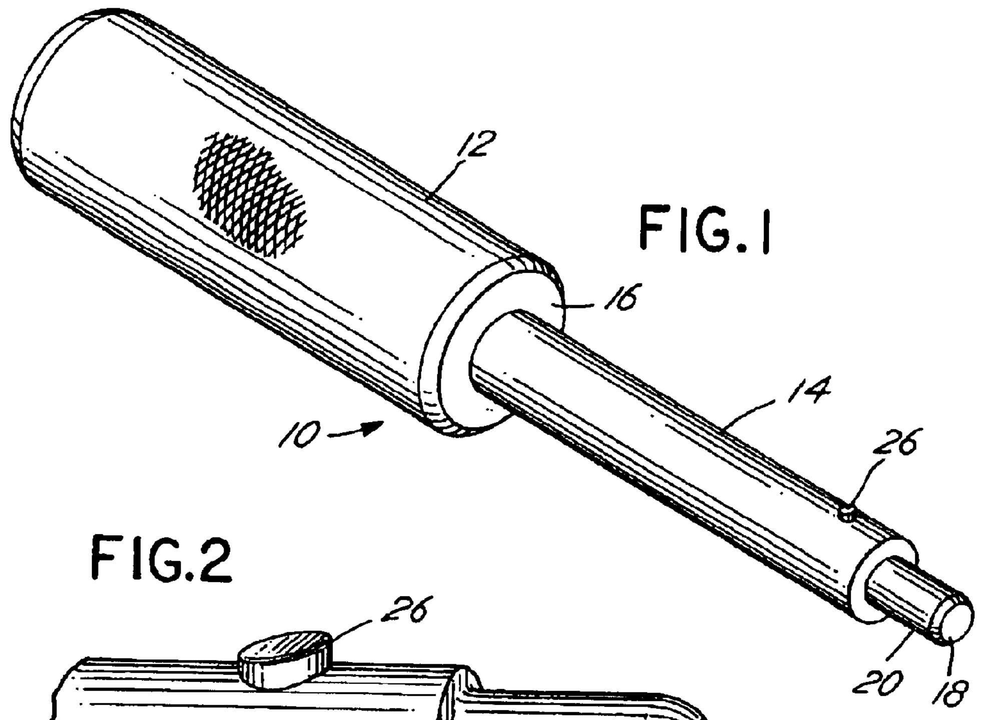
FIG. 1 is an isometric view of the insertion device of the present invention.

Referring to the figures, the present invention relates to a device for inserting an acoustical damper into a sound port of an earphone. FIG. 1 illustrates a device 10 having a handle 12 and an insertion member 14. The insertion member 14 has a diameter corresponding to the outer diameter of an acoustical cylindrical damper and includes a first end 16 and a second end 18. The first end 16 fixedly connects to the handle 12. The second end 18 forms an axially aligned damper retaining member 20. The damper retaining member 20 has an outer diameter corresponding to the inner diameter of an acoustical damper. The device 10 may be constructed of steel or other suitable rigid material. The handle 12 may be covered with rubber, textured plastic or other suitable material to aid in gripping the handle 12.

Figure 2:
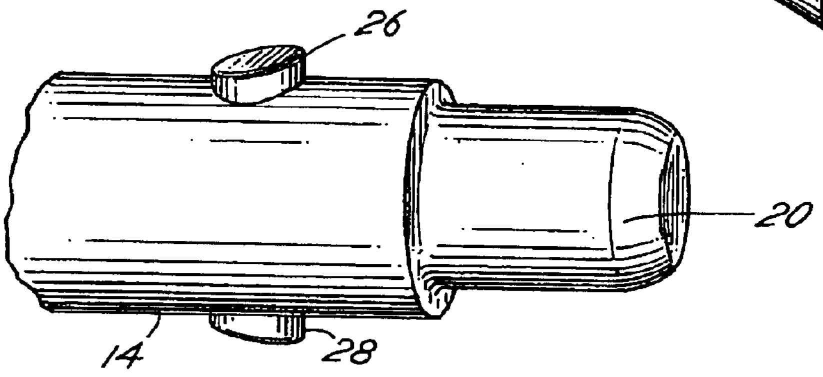
FIG. 2 depicts the insertion device of the present invention.
Figure 3:
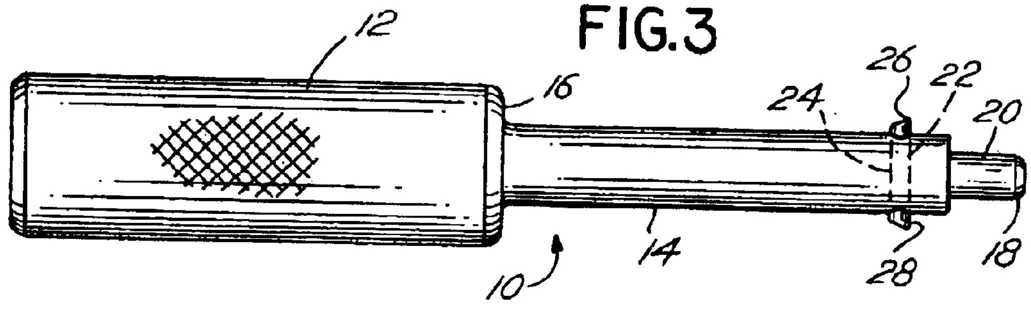
FIG. 3 is a side view of the insertion device shown in FIG. 1.
Figure 4:
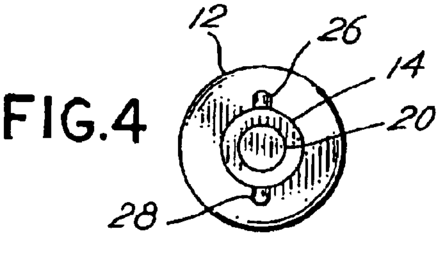
FIG. 4 is an end view of the insertion device shown in FIG. 1.

As shown in FIGS. 2, 3 and 4, a pin bore 22 located a distance from the damper retaining member 20 extends through the axial cross section of the insertion member 14. A pin 24 is press fitted into the pin bore 22 and forms material displacement members 26, 28. One of ordinary skill in the art will recognize that that the pin bore 22 and the pin 24 may be any shape, for example, circular, rectangular, square, triangular, or the like. Further, other methods can be utilized to construct the material displacement members 26, 28 on the insertion member 14, for example, welding, molding, or the like. In addition, the insertion member 14 can be constructed in such a fashion to vary the number of displacement members. For instance, an insertion member 14 can be constructed with only one displacement member, as shown in FIG. 1, or numerous displacement members, as shown in FIGS. 9, 10, and 11.

Figure 5:
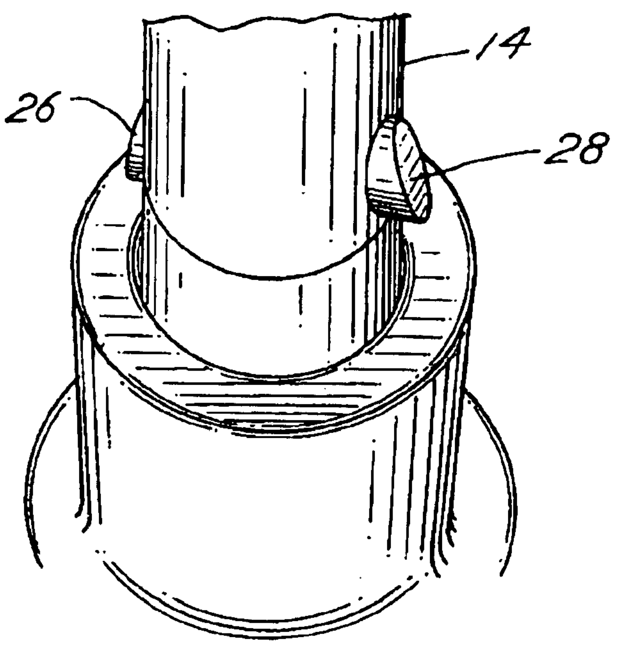
FIG. 5 depicts the insertion device shown in FIG. 1 in conjunction with an acoustical damper and a sound port.

In operation, a damper is placed on the damper retaining member 20 of the insertion member 14. As shown in FIG. 5, the outer diameter of the insertion member 14 preferably corresponds with the outer diameter of the acoustical damper. The shape of the damper retaining member 20, however, may be any shape, depending on the shape of the acoustical damper. For example, if the acoustical damper is square, the damper retaining member 20 may be square.

Figure 6:
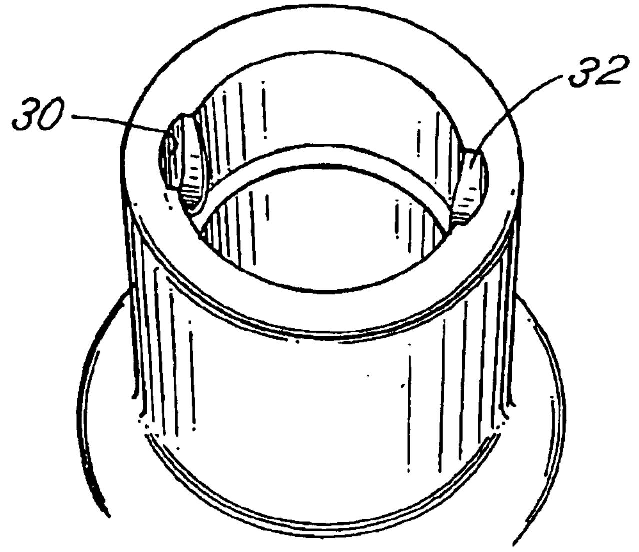
FIG. 6 depicts an acoustical damper retained in a sound port.

The damper is then inserted into the sound port by aligning the insertion member 14 with the opening of the cylindrical sound port. As the insertion member 14 guides the damper into the sound port, the displacement members 26, 28 contact the cylindrical sound port. A minimal force is applied on the sound port with the device 10 to cause the displacement members 26, 28 to displace a sufficient amount of sound port material located at the opening of the sound port. The displaced material, which is typically ABS plastic or other suitable material, form retaining notches 30, 32 in the opening of the sound port as shown in FIG. 6. The insertion member 14 is removed and the damper is retained in the sound port by the retaining notches 30, 32.

The number of retaining notches formed in a sound port is dependent on the number of displacement members on the insertion member 14. For example, FIGS. 7 and 8 illustrate an embodiment of the device 10 having a singular displacement member 34, which would form a singular retaining notch in the sound port. Another embodiment of the device 10, as shown in FIGS. 9, 10, and 11, includes multiple displacement members 36, 38, 40, and 42. The increased number of displacement members result in an increased number of retaining notches formed in the sound port. Thus, depending on the number of retaining notches desired, the device 10 may be constructed with any number of displacement members.

In addition, the location of the retaining notches may be formed at varying positions on the sound port depending on the location of the displacements members on the insertion member 14. For example, as shown in FIGS. 12, 13, and 14, the displacement members 44 and 46 may be flush with the retaining member 20. Such a construction would result in the retaining notches 30, 32 being located a distance inward from the opening of the sound port, resulting in the acoustical damper being firmly positioned in the sound port. Alternatively, in another embodiment, as illustrated in FIGS. 15, 16, and 17, the device 10 may have displacement members 48 and 50 flush with the retaining member 20 and displacement members 52 and 54 located a distance from the retaining member 20. Using this construction, as shown in FIG. 18, the displacements members 48 and 50 form retaining notches 56 and 58 located a distance inward from the opening of the sound port and the displacement members 52 and 54 form retaining notches 60 and 62 at or near the opening of the sound port. With this construction, the retaining notches 60 and 62 provide additional protection from the damper falling out of the sound port in the event that it the first two retaining notches 56 and 58 should fail.

Another embodiment of the present invention relates to a method of inserting and retaining a cylindrical acoustical damper in a cylindrical sound port. The method comprises the steps of: placing a cylindrical acoustical damper on a damper insertion device 10, wherein the damper insertion device 10 includes displacement members 26 and 28; guiding the acoustical damper into the opening of a cylindrical sound port with the insertion device 10; positioning the damper completely within the sound port with the insertion device 10; contacting the displacement members of the insertion device 10 with the cylindrical opening of the sound port; applying pressure with the displacement member to form retaining notches in the opening of the sound port;

retaining the acoustical damper within the sound port with the retaining notches.

It will be recognized by those skilled in the art that the illustrated embodiments can be modified in arrangement and detail without departing from the scope of the present invention. Therefore, to particularly point out and distinctly claim the subject matter regarded as the invention, the following claims conclude the specification.

I claim:

1. A damper insertion device comprising:

an insertion member having a retaining member for inserting an acoustical damper into a sound port, the insertion member having at least one displacement member for forming at least one retaining notch in the sound port.

2. The damper insertion device of claim 1 wherein the retaining member is cylindrical and has an outer diameter corresponding to an inner diameter of the acoustical damper.

3. The damper insertion device of claim 1 wherein the insertion member is cylindrical and has an outer diameter corresponding to an outer diameter of the acoustical damper.

4. A damper insertion device comprising:

a device handle;

an insertion member having a first end and a second end, wherein the second end fixedly connects to the device handle and the second ends forms a retaining member for retaining an acoustical damper on the insertion member; and at least one displacement member located on the insertion member for forming at least one retaining notch in a sound port.

5. A method of inserting and retaining an acoustical damper in a sound port of an earphone comprising:

providing a damper insertion device having a retaining member and at least one displacement member;

placing an acoustical damper on the retaining member of the insertion device;

guiding the acoustical damper into a opening of a sound port with the insertion device;

positioning the acoustical damper completely within the sound port with the insertion device;

contacting the at least one displacement member with the sound port;

applying a force with the at least one displacement member to form at least one retaining notch in the sound port; and retaining the acoustical damper within the sound port with the retaining notch.

6. The method of inserting and retaining an acoustical damper in a sound port of an earphone of claim 4 wherein the retaining notch is located at or near the opening of the sound port.

7. The method of inserting and retaining an acoustical damper in a sound port of an earphone of claim 5 wherein the retaining notch is located a distance inward from the opening of the sound port.

8. The method of inserting and retaining an acoustical damper in a sound port of an earphone of claim 5 wherein the retaining member is cylindrical and has an outer diameter corresponding to the inner diameter of the acoustical damper.

9. The method of inserting and retaining an acoustical damper in a sound port of an earphone of claim 5 wherein the insertion member is cylindrical and has an outer diameter corresponding to the outer diameter of an acoustical damper.

10. A method of retaining an acoustical damper in a sound port of an earphone comprising:

providing an insertion member having at least one displacement member;

contacting a sound port with the at least one displacement member; and applying a force with the at least one displacement member to form at least one retaining notch in the sound port for retaining an acoustical damper within the sound port.

* * * * *

UNITED STATES PATENT AND TRADEMARK OFFICE

CERTIFICATE OF CORRECTION

PATENT NO. : 6,772,854 B2 Page 1 of 1
DATED : August 10, 2004
INVENTOR(S) : John James Wubker It is certified that error appears in the above-identified patent and that said Letters Patent is hereby corrected as shown below:

Column 4,
Line 35, please delete “replacements” and insert therfor -- replacement. --
Line 48, please delete “56 and 58” and insert therefor -- 60 and 62. --
Line 50, please delete “60 and 62” and insert therefor -- 56 and 58. --
Line 54, please delete the word “it” preceding the word “the.”

Signed and Sealed this

Thirtieth Day of November, 2004

JON W. DUDAS
*Director of the United States Patent and Trademark Office*